(12) United States Patent
Boylan

(10) Patent No.: US 10,792,408 B2
(45) Date of Patent: Oct. 6, 2020

(54) MEDICAL FLUID THERAPY MACHINE INCLUDING READILY ACCESSIBLE PNEUMATIC MANIFOLD AND VALVES THEREFORE

(71) Applicants: Baxter International Inc., Deerfield, IL (US); Baxter Healthcare SA, Glattpark (Opfikon) (CH)

(72) Inventor: Charles Wayne Boylan, St. Louis, MO (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 579 days.

(21) Appl. No.: 15/336,247

(22) Filed: Oct. 27, 2016

(65) Prior Publication Data

US 2018/0117232 A1    May 3, 2018

(51) Int. Cl.

| | |
|---|---|
| *A61M 1/14* | (2006.01) |
| *A61M 1/26* | (2006.01) |
| *A61M 1/10* | (2006.01) |
| *A61M 1/36* | (2006.01) |
| *F16L 15/00* | (2006.01) |
| *A61M 1/28* | (2006.01) |
| *A61M 1/34* | (2006.01) |

(Continued)

(52) U.S. Cl.
CPC .......... *A61M 1/267* (2014.02); *A61M 1/1006* (2014.02); *A61M 1/14* (2013.01); *A61M 1/28* (2013.01); *A61M 1/34* (2013.01); *A61M 1/367* (2013.01); *A61M 39/22* (2013.01); *F04B 43/073* (2013.01); *F16L 15/008* (2013.01); *A61M 1/3413* (2013.01); *A61M 1/3496* (2013.01)

(58) Field of Classification Search
CPC .... A61M 1/267; A61M 1/1006; A61M 1/367; F16L 15/00; F16L 15/006; F16L 15/008
USPC .................................................... 251/129.15
See application file for complete search history.

(56) References Cited

U.S. PATENT DOCUMENTS 4,610,267 A * 9/1986 Beck et al. ........... F16K 11/048
  137/596.17
2015/0013799 A1    1/2015 Sarai et al.

FOREIGN PATENT DOCUMENTS

WO    03/023270 A1    3/2003

OTHER PUBLICATIONS

International Search Report and Written Opinion for related International Application No. PCT/US2017/058744; report dated Apr. 17, 2018; (21 pages).

* cited by examiner

*Primary Examiner* — Kevin L Lee
(74) *Attorney, Agent, or Firm* — K&L Gates LLP

(57) ABSTRACT

A connection apparatus for sealing to a pathway of a mounting structure includes a body; and a port including a threaded portion extending from the body and a non-threaded portion extending from the threaded portion, the non-threaded portion carrying a gasket, the gasket positioned along the non-threaded portion such that the mounting structure to which the connection apparatus is mounted contacts the gasket prior to the threaded portion engaging a mating threaded portion of the mounting structure, the port providing fluid communication between the body and the pathway of the mounting structure. The body may be that of a valve that supplies any of air, water or oil as an operating fluid to, for example, inlet and outlet valves and a pump chamber of a medical fluid pump of a medical fluid delivery machine.

16 Claims, 9 Drawing Sheets

(51) Int. Cl.
*A61M 39/22* (2006.01)
*F04B 43/073* (2006.01)

MEDICAL FLUID THERAPY MACHINE INCLUDING READILY ACCESSIBLE PNEUMATIC MANIFOLD AND VALVES THEREFORE

BACKGROUND

The present disclosure relates generally to devices, systems and methods for medical fluid delivery machines. More specifically, the present disclosure relates to medical fluid delivery machines, such as renal failure therapy machines, that employ pneumatic pumping.

Regarding renal failure therapy machines, due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that frequent treatments remove more toxins and waste products than a patient receiving less frequent but perhaps longer treatments. A patient receiving more frequent treatments does not experience as much of a down cycle as does an in-center patient, who has built-up two or three days' worth of toxins prior to a treatment. In certain areas, the closest dialysis center can be many miles from the patient's home causing door-to-door treatment time to consume a large portion of the day. HHD may take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

Any of the above modalities performed by a machine may employ pneumatic pumping. Pneumatic pumping typically involves the application of positive and/or negative air pressure to a pumping membrane or diaphragm and to associated valve membranes or diaphragms. Positive pressure may be provided via a compressor feeding a positive pressure tank or accumulator. Negative pressure may be provided via a vacuum pump feeding a negative pressure tank or accumulator.

The positive and negative pressure tanks are separated from the pumping and valve membranes via pneumatic valves, which are generally electrically actuated pneumatic valves. The pneumatic valves may be binary or on/off solenoid valves, which may be spring-closed and electrically opened by energizing the winding of the solenoid. The pneumatic valves may alternatively be variable orifice valves, which are opened or closed in an analog manner based upon an amount of electrical energy delivered to the valve.

The pneumatic valves operate with air passageways. It is important first off to seal the valves around the passageways, so that air does not leak into or out of the passageways from or to atmosphere. In sealing the valves around the passageways, however, care should be taken so that material from the valve or from a mounting of the valve does not fall into or otherwise enter the passageways, which may negatively effect operation of the valves and/or cause damage.

In addition, the pneumatic valves may wear out or require replacement over time, e.g., due to a service schedule. While it is a goal typically to have a compact machine, the valves should be readily accessible, so that they can be individually removed and replaced if needed.

SUMMARY

In one primary embodiment, a connection apparatus is provided. The connection apparatus is formed with a body. The body may be that of any type of fluid control component including but not limited to a variable orifice valve body, a binary valve body, a pressure gauge body, a pressure regulator body, a flowmeter body, a filter body, piping, tubing and/or associated fittings. The fluid may be any type of working fluid including air, liquid, such as water, hydraulic or oil. In each instance, the connection apparatus prevents the introduction of particulates during attachment of the connection apparatus and associated body to a mounting structure, such as a pneumatic pressure manifold.

The connection apparatus in an embodiment includes a port having a threaded portion extending from the body and a non-threaded portion (e.g., smooth) extending from the threaded portion. The non-threaded portion carries a gasket, such as an o-ring gasket, positioned along the non-threaded portion such that the mounting structure to which the connection apparatus is mounted contacts the gasket prior to the threaded portion engaging a mating threaded portion of the mounting structure. The threaded connection is thereby sealed off from the fluid pathway prior to the connection being made. Any chips or debris coming loose due to threading of the connection apparatus to the mounting structure are thereby trapped by the o-ring and do not fall into the fluid pathway. The port thereafter allows fluid communication between the fluid pathway and the body.

The above connection apparatus and others disclosed herein may be used for example with pneumatic manifolds for medical fluid treatments such as: plasmapheresis, hemodialysis ("HD"), hemofiltration ("HF") hemodiafiltration ("HDF"), and continuous renal replacement therapy ("CRRT") treatments. The apparatuses, manifolds, systems and methods described herein are also applicable to peritoneal dialysis ("PD") and to intravenous drug delivery. These modalities may be referred to herein collectively or generally individually as medical fluid delivery.

Moreover, each of the devices, systems and methods described herein may be used with clinical or home-based machines. For example, the systems may be employed in in-center HD, HF or HDF machines, which run throughout the day. Alternatively, the systems may be used with home HD, HF or HDF machines, which are operated at the patient's convenience. One such home system is described in U.S. Pat. No. 8,029,454 ("the '454 Patent"), issued Oct. 4, 2011, entitled "High Convection Home Hemodialysis/Hemofiltration And Sorbent System", filed Nov. 4, 2004, assigned to the assignee of the present application. Another such home system is described in U.S. Pat. No. 8,393,690 ("the '690 Patent"), issued Mar. 12, 2013, entitled "Enclosure for a Portable Hemodialysis System", filed Aug. 27, 2008. The entire contents of each of the above references are incorporated herein by reference and relied upon.

In an embodiment, a medical fluid delivery machine is provided that includes a medical fluid delivery chassis. The medical fluid delivery chassis houses components needed to deliver medical fluid, such as one or more pump, plural valves, a heater if needed, online medical fluid generation equipment if needed and desired, plural sensors, such as any one, or more, or all of pressure sensors, conductivity sensors, temperature sensors, air detectors, blood leak detectors, and the like, a user interface, and a control unit, which may employ one or more processor and memory to control the above-described equipment.

Various components, such as the fluid pumps and valves, may be actuated pneumatically. In such a case, it is contemplated to provide a pneumatic manifold, which houses binary solenoid and/or variable pneumatic valves that selectively allow positive or negative pressure air to reach desired locations, such as the air side of a pump or valve membrane. "Air" as used herein means air as it exists naturally, which is made up of individual gases such as nitrogen, oxygen, argon, and carbon dioxide. "Air" may also include a desired modified atmosphere, such as a larger percentage of, or a pure gas, such nitrogen or carbon dioxide. The term "pneumatic" also refers to naturally occurring air and/or any type of modified atmosphere.

The pneumatic valves of the manifold receive positive and/or negative pressure air from one or more positive and/or negative pressure air accumulator. For example, the machine may include a high positive accumulator, a low positive accumulator, and one or more negative pressure accumulator. The positive pressure accumulators are pressurized via a compressor running air through a dryer. The one or more negative pressure accumulator is pressurized via a vacuum pump.

The manifold is mounted inside the chassis of the machine via a mounting assembly. Outside of the manifold is a faceplate connected to the mounting assembly in one embodiment. The faceplate provides quick pneumatic coupling between the positive and negative pressure accumulators and the pneumatic manifold in one embodiment. To that end, the faceplate may be connected to the pneumatic manifold via pneumatic lines or tubing, which may be flexible or rigid as even rigid pneumatic tubing will be flexible enough to allow for the faceplate movement described below. The faceplate in an embodiment also includes quick connection to power connections, such as alternating current ("AC") power connections and direct current ("DC") power connections. To that end, the faceplate may be further connected to flexible electrical lines leading to necessary places within the machine.

In one embodiment, the mounting assembly includes a fixed portion fixed to the machine and the faceplate, which is a removable portion fixed to the fixed portion. The fixed portion for example may include first and second flanges that are bolted to the machine chassis and the pneumatic manifold to support the manifold. The removable portion or faceplate is in one embodiment located between and bolted to the first and second flanges. The quick connections to the pressure accumulators and the power lines are provided in an embodiment on an outwardly facing surface of the removable faceplate, while the pneumatic lines to the pneumatic manifold and flexible power lines to the machine are provided on an inwardly facing surface of the removable faceplate.

If needed, the removable faceplate may be unbolted from the fixed portion and swung out of the way so that a service person can gain access to pneumatic valves attached to the pneumatic manifold. Providing ready access to the pneumatic manifold enables the pneumatic valves to be replaced easily without having to remove or move the pneumatic manifold itself. Once replaced, the removable faceplate may be swung back into position against the fixed portion and reattached.

As discussed above, there may be different types of pneumatic valves connected to the pneumatic manifold, such as binary (on-off) valves and variable orifice valves (vari-valves). The valves and in particular the vari-valves may seal to a surface of a plate of the pneumatic manifold. The seal generally involves sealing around two holes in the plate and two orifices in the valve, namely, an air inlet hole/orifice and an air outlet hole/orifice. The valve in an embodiment includes two o-rings, namely, a central o-ring sealing a centrally located valve orifice and an outer o-ring, sealing an offset valve orifice in combination with the centrally located o-ring. The present disclosure provides different embodiments for sealing the pneumatic valves to a plate of the pneumatic manifold.

In one embodiment, a clamping bracket is provided, which compresses the valve to the plate of the pneumatic manifold, thereby compressing the inner and outer o-rings. The clamping bracket may be made of metal or of tough plastic, such as teflon. The clamping bracket in an embodiment fits around and contacts a valve diameter located in roughly the middle of the valve, leaving a top, electrical contact portion of the valve exposed to receive electrical wires. The clamping bracket may therefore be provided in two or more pieces or members, which come together from opposing sides of the valve and extend around the valve diameter. In this manner, the force from the clamping bracket is distributed evenly across the valve, so that the valve is not tilted during compression and so that the o-rings are compressed evenly.

The clamping bracket may be secured to the manifold plate by fastening the bracket members into the plate of the pneumatic manifold adjacent to the pneumatic valve. The bracket provides a flange having one or more mounting hole that aligns with one or more threaded hole in the plate. In this manner, the pneumatic valve may be easily replaced by unfastening the bracket members or unfastening one bracket member and loosening the other. The fastening brackets allow the valve to be affixed to the manifold, compressing the sealing o-rings without introducing contaminates associated with the mating of threaded components into the pneumatic path.

In other embodiments, the pneumatic valves are threaded into a plate of the pneumatic manifold. Here, problems may occur because the threading has the potential of shearing off and introducing particulate material into the pneumatic pathways and lines. In certain embodiments, the threads of the pneumatic valve may be stainless steel, which may be a relatively hard material compared to that of the manifold plate, which may be aluminum. Hence, shearing of the softer aluminum may occur. Introduction of particulate material into the pneumatic pathways or lines may cause premature failure of the elements of the overall pneumatic system, such as the pneumatic valves, fluid valve chamber or fluid pump chambers.

It is accordingly contemplated to provide a seal that seals the threaded engagement from the rest of the pneumatic system prior to the threaded engagement taking place. In one embodiment, the pneumatic valve is provided with a port, which is threaded adjacent to the valve body and which extends to a smooth section. The mating aperture formed in the plate of the pneumatic manifold likewise includes a mating threaded portion adjacent to a surface of the plate that extends to a mating smooth section. A gasket, such as an o-ring gasket, is fitted either onto the smooth section of the valve port or into the smooth section of the aperture formed in the plate of the pneumatic manifold. When securing the valve to the manifold, the mating smooth portions of the valve port and the plate aperture compress the gasket prior to the threaded engagement between the port and the aperture. In this manner, a protective seal is formed between the pneumatic system and the threaded connection prior to the contact of male and female threaded parts. The protective seal prevents particulates that may generated by contact of male and female threaded parts from entering the pneumatic system.

If the gasket is fitted to the port of the valve, the smooth portion of the port may be provided with a groove that seats the gasket. If the gasket is instead placed into the aperture of the manifold plate, the gasket may be seated against a stop formed or placed into the aperture. In either case, the gasket is held securely when compressed. The gasket is a first gasket. As discussed above, the valve body may be equipped with one or more additional gaskets to seal around one or more orifice formed in the valve body.

The medical fluid machine of the present disclosure in one embodiment places the pneumatic pumping components, such as a compressor and associated dryer, vacuum pump, at least one positive pressure accumulator and at least one negative pressure accumulator in a pneumatic pump box. The pneumatic pump box may be connected removeably to medical fluid delivery chassis, so that the pump box can be moved away from the patient to reduce noise. Plural pneumatic and power lines may run from the pneumatic pump box to a medical fluid delivery chassis of the machine.

In an embodiment, the removed pump box exposes a backside of the medical fluid delivery chassis and an access door. The access door is removable to expose a removable electronics cage. The electronics cage holds multiple printed circuit boards ("PCB's"), and other electrical equipment of the medical fluid machine. Electronics cage is constructed to provide (i) physical shock and vibration support to the unit's PCB's and (ii) electromagnetic shielding for the electrical components. The electronics cage is positioned to prevent heat generated from the unit's internal hot elements from being transferred to the electronics cage. The electronics cage is in one embodiment also configured to allow adequate airflow to the PCB's to prevent their premature failure due to excessive heat.

In an embodiment, the electronics cage is electrically attached to the medical fluid machine, so that the machine can continue to function even when the electronics cage is removed completely from the interior of the device. Such functionality allows a service person to have better access to the PCB's and fluid components within the machine during service activities, such as diagnostic testing. Electrical components that are not held within electronics cage include a power supply and other electrical equipment that generate heat, such as transformers (which may be part of the power supply). By doing so, heat generated by the power supply, etc., does not become trapped within the electronics cage.

Providing an electronics cage and hinging it out of the way also enables the PCB's and other electrical equipment of the machine to be held in place firmly, increasing reliability. The removable electronics cage also improves the serviceability of machine, regarding both the contents of the cage and by opening up the interior space within the machine, allowing better access to other machine components.

In light of the disclosure herein and without limiting the disclosure in any way, in a first aspect of the present disclosure, which may be combined with any other aspect listed herein unless specified otherwise, a medical fluid delivery machine includes: a medical fluid pump including a pneumatically actuated pump chamber and first and second pneumatically actuated medical fluid valve chambers located respectively upstream and downstream of the pneumatically actuated pump chamber; at least one of a positive air pressure source or a negative air pressure source for supplying positive or negative pressure air, respectively, to at least one of the pneumatically actuated pump chamber, the first pneumatically actuated medical fluid valve chamber, or the second pneumatically actuated medical fluid valve chamber; a pneumatic manifold including an air passageway in fluid communication with (i) at least one of the pneumatically actuated pump chamber, the first pneumatically actuated medical fluid valve chamber, or the second pneumatically actuated medical fluid valve chamber and (ii) the at least one positive or the negative air pressure source, the pneumatic manifold defining a manifold aperture; and a pneumatic valve defining a valve aperture sized and arranged such that when the pneumatic valve is abutted against the pneumatic manifold, the valve aperture mates with the manifold aperture, the pneumatic valve including a gasket that extends around the valve aperture; and a bracket configured to clamp the pneumatic valve to the pneumatic manifold, compressing the gasket to seal the pneumatic valve to the manifold.

In a second aspect of the present disclosure, which may be combined with any other aspect listed herein unless specified otherwise, the bracket is removeably fastened to the pneumatic manifold.

In a third aspect of the present disclosure, which may be combined with any other aspect listed herein unless specified otherwise, the bracket fits around a diameter of the pneumatic valve so as to expose an upper electrical connection portion of the pneumatic valve.

In a fourth aspect of the present disclosure, which may be combined with any other aspect listed herein unless specified otherwise, the bracket includes plural members that each fit around a diameter of the pneumatic valve.

In a fifth aspect of the present disclosure, which may be combined with the fourth aspect in combination with any other aspect listed herein unless specified otherwise, the plural members abut each other when fitted around the diameter of the pneumatic valve.

In a sixth aspect of the present disclosure, which may be combined with the fourth aspect in combination with any other aspect listed herein unless specified otherwise, the plural members are configured to spread a holding force around the pneumatic valve.

In a seventh aspect of the present disclosure, which may be combined with any other aspect listed herein unless specified otherwise, the valve aperture is a first valve aperture, and which includes a second valve aperture and a second gasket, the first and second gaskets sealing around the second valve aperture via the clamping of the bracket.

In an eighth aspect of the present disclosure, which may be combined with the seventh aspect in combination with any other aspect listed herein unless specified otherwise, the first valve aperture is located along a central axis of the pneumatic valve, while the second valve aperture is spaced away from the central axis.

In a ninth aspect of the present disclosure, which may be combined with the seventh aspect in combination with any other aspect listed herein unless specified otherwise, the first and second gaskets are o-ring gaskets.

In a tenth aspect of the present disclosure, which may be combined with any other aspect listed herein unless specified otherwise, a medical fluid delivery machine includes: a medical fluid pump including a pneumatically actuated pump chamber and first and second pneumatically actuated medical fluid valve chambers located respectively upstream and downstream of the pneumatically actuated pump chamber; at least one of a positive air pressure source or a negative air pressure source for supplying positive or negative pressure air, respectively, to at least one of the pneumatically actuated pump chamber, the first pneumatically actuated medical fluid valve chamber, or the second pneumatically actuated medical fluid valve chamber; a pneumatic manifold including an air passageway in fluid communication with (i) at least one of the pneumatically actuated pump chamber, the first pneumatically actuated medical fluid valve chamber, or the second pneumatically actuated medical fluid valve chamber and (ii) the at least one positive or the negative air pressure source, the pneumatic manifold defining an aperture including a threaded portion; a gasket; and a pneumatic valve including a pneumatic port having a mating threaded portion and a smooth portion, the pneumatic port sized and arranged such that when the pneumatic valve is connected to the pneumatic manifold, the smooth portion contacts the gasket prior to the mating threaded portion of the valve engaging the threaded portion of the aperture.

In an eleventh aspect of the present disclosure, which may be combined with the tenth aspect in combination with any other aspect listed herein unless specified otherwise, the smooth portion of the pneumatic port is sized and arranged to seal to an inner diameter of the gasket, while an outer diameter of the gasket seals to a surface of the aperture.

In a twelfth aspect of the present disclosure, which may be combined with the tenth aspect in combination with any other aspect listed herein unless specified otherwise, the gasket is located initially in the aperture.

In a thirteenth aspect of the present disclosure, which may be combined with the twelfth aspect in combination with any other aspect listed herein unless specified otherwise, the gasket is seated against a stop in the aperture, the stop having an inner diameter less than an inner diameter of the threaded portion of the aperture.

In a fourteenth aspect of the present disclosure, which may be combined with the tenth aspect in combination with any other aspect listed herein unless specified otherwise, the gasket is located initially on the smooth portion of the pneumatic port.

In a fifteenth aspect of the present disclosure, which may be combined with the fourteenth aspect in combination with any other aspect listed herein unless specified otherwise, the gasket is located within a groove formed in the smooth portion of the pneumatic port.

In a sixteenth aspect of the present disclosure, which may be combined with the fourteenth aspect in combination with any other aspect listed herein unless specified otherwise, the aperture includes the threaded portion and a smooth portion, the gasket extending through the threaded portion and sealing against the smooth portion of the aperture when the pneumatic valve is connected to the pneumatic manifold.

In a seventeenth aspect of the present disclosure, which may be combined with the tenth aspect in combination with any other aspect listed herein unless specified otherwise, the pneumatic valve defines an aperture, the gasket a first gasket, and which includes a second gasket extending around an outside of the aperture, the second gasket compressed when the pneumatic valve is connected to the pneumatic manifold.

In an eighteenth aspect of the present disclosure, which may be combined with any other aspect listed herein unless specified otherwise, a medical fluid delivery machine includes: a medical fluid pump including a pneumatically actuated pump chamber and first and second pneumatically actuated medical fluid valve chambers located respectively upstream and downstream of the pneumatically actuated pump chamber; at least one of a positive air pressure source or a negative air pressure source for supplying positive or negative pressure air, respectively, to at least one of the pneumatically actuated pump chamber, the first pneumatically actuated medical fluid valve chamber, or the second pneumatically actuated medical fluid valve chamber; a pneumatic manifold including a plurality of pneumatic valves in fluid communication with (i) at least one of the pneumatically actuated pump chamber, the first pneumatically actuated medical fluid valve chamber, or the second pneumatically actuated medical fluid valve chamber and (ii) the at least one positive or the negative air pressure source; and a faceplate connected to the manifold via at least one pneumatic line, the faceplate configured to provide quick pneumatic connection to the at least one of the positive air pressure source or the negative air pressure source, the faceplate being removable so that the faceplate can be moved out of the way to access at least some of the plurality of pneumatic valves.

In a nineteenth aspect of the present disclosure, which may be combined with the eighteenth aspect in combination with any other aspect listed herein unless specified otherwise, the machine includes a machine frame and a mounting assembly attached to the machine frame and mounting the pneumatic manifold, and wherein the mounting assembly includes a fixed portion fixed to the machine frame, the faceplate attached removeably to the fixed portion.

In a twentieth aspect of the present disclosure, which may be combined with the nineteenth aspect in combination with any other aspect listed herein unless specified otherwise, the fixed portion includes first and second mounting flanges, the faceplate located between the first and second mounting flanges.

In a twenty-first aspect of the present disclosure, which may be combined with the nineteenth aspect in combination with any other aspect listed herein unless specified otherwise, the fixed portion is bolted to the frame and the faceplate is bolted to the fixed portion.

In a twenty-second aspect of the present disclosure, which may be combined with the eighteenth aspect in combination with any other aspect listed herein unless specified otherwise, the faceplate is configured to provide quick pneumatic connection to multiple positive air pressure sources and multiple negative air pressure sources.

In a twenty-third aspect of the present disclosure, which may be combined with the eighteenth aspect in combination with any other aspect listed herein unless specified otherwise, the faceplate is configured to provide quick electrical connection, the faceplate connected additionally to electrical lines running to the machine.

In a twenty-fourth aspect of the present disclosure, which may be combined with any other aspect listed herein unless specified otherwise, a connection apparatus for sealing to a pathway of a mounting structure includes: a body; and a port including a threaded portion extending from the body and a non-threaded portion extending from the threaded portion, the non-threaded portion carrying a gasket, the gasket positioned along the non-threaded portion such that the mounting structure to which the connection apparatus is mounted contacts the gasket prior to the threaded portion engaging a mating threaded portion of the mounting structure, the port providing fluid communication between the body and the pathway of the mounting structure.

In a twenty-fifth aspect of the present disclosure, which may be combined with the twenty-fourth aspect in combination with any other aspect listed herein unless specified otherwise, the body is a valve body, the valve body configured to be electrically actuated to move a member to open or close a fluid passageway, the member and the passageway located within the valve body.

In a twenty-sixth aspect of the present disclosure, which may be combined with the twenty-fourth aspect in combination with any other aspect listed herein unless specified otherwise, the non-threaded portion defines a groove that accepts the gasket.

In a twenty-seventh aspect of the present disclosure, which may be combined with the twenty-fourth aspect in combination with any other aspect listed herein unless specified otherwise, the body includes a surface, the port extending from the surface, the surface defining an aperture spaced apart from the port, the gasket a first gasket, and wherein the valve body includes a second gasket extending around the spaced-apart aperture.

In a twenty-eighth aspect of the present disclosure, which may be combined with the twenty-fourth aspect in combination with any other aspect listed herein unless specified otherwise, the connection apparatus is configured for use with a pneumatic, water or oil-based system.

In a twenty-ninth aspect of the present disclosure, which may be combined with the twenty-fourth aspect in combination with any other aspect listed herein unless specified otherwise, the body is a variable orifice valve body, a binary valve body, a pressure gauge body, a pressure regulator body, a flowmeter body, a filter body, piping, tubing, or a piping/tubing fitting.

In a thirtieth aspect of the present disclosure, any of the structure and functionality disclosed in connection with FIGS. 1 to 10 may be combined with any of the other structure and functionality disclosed in connection with FIGS. 1 to 10.

In light of the present disclosure and the above aspects, it is therefore an advantage of the present disclosure to provide an improved medical fluid delivery device.

It is another advantage of the present disclosure to provide an improved pneumatic manifold for a medical fluid delivery device.

It is a further advantage of the present disclosure to provide a pneumatic manifold for a medical fluid delivery device that properly seals the pneumatic valves to the manifold.

It is still another advantage of the present disclosure to provide a pneumatic manifold for a medical fluid delivery device that attempts to maintain particulate-free air passageways leading to and from the pneumatic valves.

It is still a further advantage of the present disclosure to provide a pneumatic manifold that allows ready access to the pneumatic valves for repair and replacement.

It is yet another advantage of the present disclosure to maintain sensitive electronic equipment in a cooler environment.

It is yet a further advantage of the present disclosure to provide ready access to sensitive electronic equipment and to other components within the medical fluid machine chassis.

Further still, it is an advantage of the present disclosure to provide a high temperature air detector with consolidated electronics.

The advantages discussed herein may be found in one, or some, and perhaps not all of the embodiments disclosed herein. Additional features and advantages are described herein, and will be apparent from, the following Detailed Description and the figures.

DETAILED DESCRIPTION

The examples described herein are applicable to any medical fluid delivery system that delivers a medical fluid, such as blood, dialysis fluid, substitution fluid or and intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as renal failure therapy. Moreover, the machines and any of the pneumatically operated systems and methods described herein may be used in clinical or home settings. For example, a machine including a pneumatic manifold of the present disclosure may be employed in an in-center HD machine, which runs virtually continuously throughout the day. Alternatively, the pneumatic manifold and other features of the present disclosure may be used in a home HD machine, which can for example be run at night while the patient is sleeping. Moreover, each of the renal failure therapy examples described herein may employ a diffusion membrane or filter, such as a dialyzer, e.g., for HD or HDF, or a hemofilter, e.g., for HF.

Figure 1:
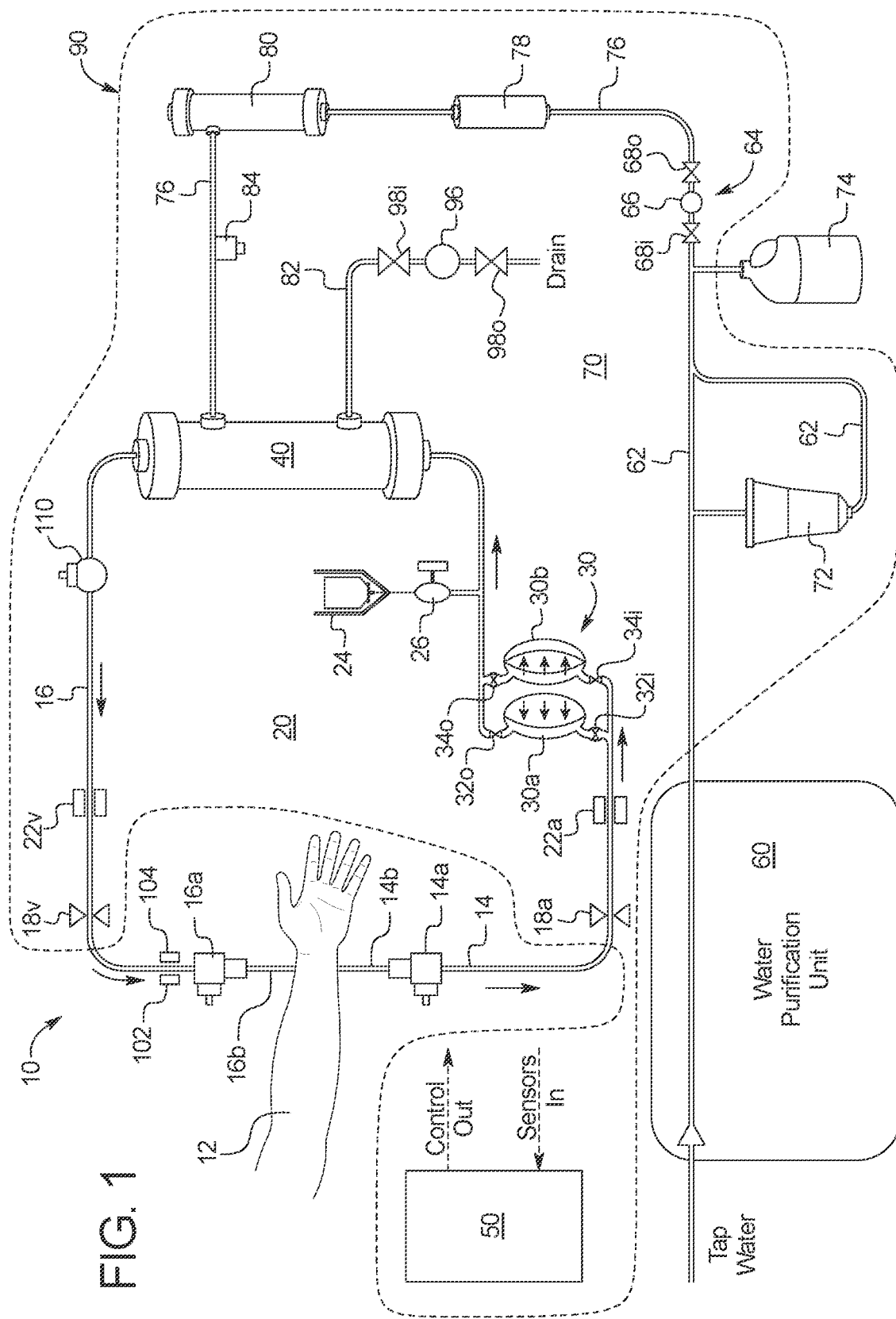
FIG. 1 is a schematic illustration of one embodiment of a renal failure therapy operated by a machine employing a pneumatic manifold mounting pneumatic valves of the present disclosure.

Referring now to FIG. 1, an example of an HD flow schematic for a medical fluid delivery system 10 employing a pneumatic manifold and other features of the present disclosure is illustrated. Because the HD system of FIG. 1 is relatively complicated, FIG. 1 and its discussion also provide support for any of the renal failure therapy modalities discussed above and for an IV machine. Generally, system 10 is shown having a very simplified version of a dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

System 10 of FIG. 1 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw communication with patient 12. Venous line 16 includes a venous line connector 16a that connects to a venous needle 16b, which is in blood return communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Figure 2:
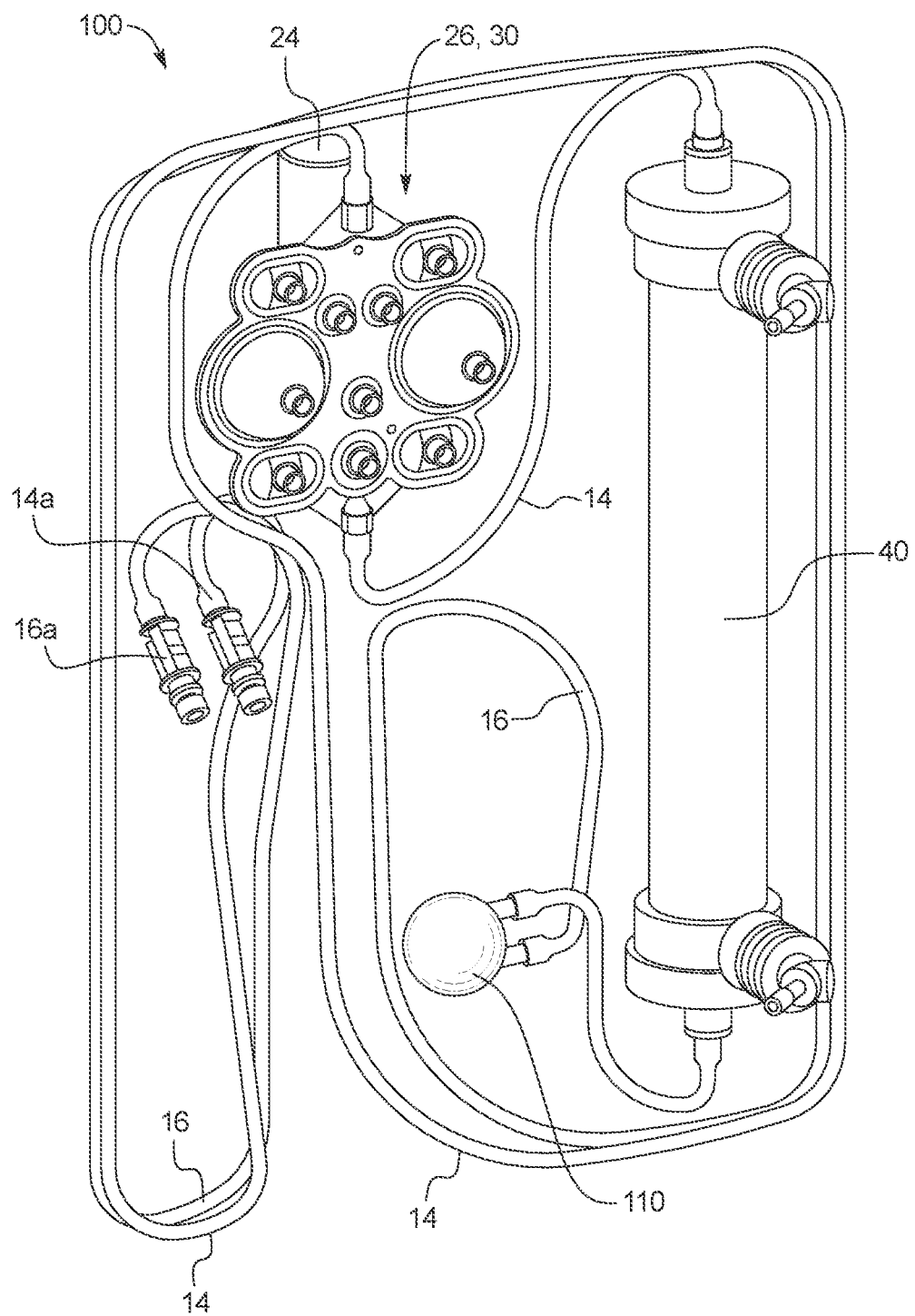
FIG. 2 is a perspective view illustrating a blood set for use with the renal failure therapy machine of FIG. 1.

Arterial and venous lines 14 and 16 also include air or bubble detectors 22a and 22v, respectively, which can be ultrasonic air detectors. Air or bubble detectors 22a and 22v look for air in the arterial and venous lines 14 and 16, respectively. If air is detected by one of air detectors 22a and 22v, system 10 closes line clamps 18a and 18v, pauses the blood and dialysis fluid pumps, and provides instructions to the patient to clear the air so that treatment can resume. In an embodiment, air detectors 22a and 22v are made of aircraft grade materials that allow the sensors to operate in a high temperature environment. FIG. 2 illustrates arterial and venous lines 14 and 16, respectively, which between treatments receive high temperature disinfecting water in one embodiment. Air detectors 22a and 22v touch lines 14 and 16 for operation and thereby become heated upon disinfection. Forming air detectors 22a and 22v and associated electronics such that they my operate in heated environments of, e.g., 105° C., enables system 10 and machine 90 to consolidate several electronic assemblies into one small integrated assembly near detectors 22a and 22v, increasing the reliability of system 10, while reducing its cost.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 tube.

A heparin vial 24 and heparin pump 26 are located between blood pump 30 and blood filter 40 (e.g., dialyzer) in the illustrated embodiment. Heparin pump 26 may be a pneumatic pump or a syringe pump (e.g., stepper motor driven syringe pump). Supplying heparin upstream of blood filter 40 helps to prevent clotting of the filter's membranes.

A control unit 50 includes one or more processor and memory. Control unit 50 receives air detection signals from air detectors 22a and 22v (and other sensors of system 10, such as temperature sensors, blood leak detectors, conductivity sensors, pressure sensors, and access disconnection transducers 102, 104), and controls components such as line clamps 18a and 18v, blood pump 30, heparin pump 26, and the dialysis fluid pumps. Blood that exits blood filter 40 via venous line 16 flows through an airtrap 110. Airtrap 110 removes air from the blood before the dialyzed blood is returned to patient 12 via venous line 16.

With the hemodialysis version of system 10 of FIG. 1, dialysis fluid or dialysate is pumped along the outside of the membranes of blood filter 40, while blood is pumped through the insides of the blood filter membranes. Dialysis fluid or dialysate is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structures to purify tap water (e.g., remove pathogens and ions such as chlorine), so that the water is in one implementation below 0.03 endotoxin units/ml ("EU/ml") and below 0.1 colony forming units/ml ("CFU/ml"). Water purification unit 60 may be provided in a housing separate from the housing or chassis of the hemodialysis machine, which includes blood circuit 20 and a dialysis fluid circuit 70.

Dialysis fluid circuit 70 is again highly simplified in FIG. 1 to ease illustration. Dialysis fluid circuit 70 in actuality may include all of the relevant structure and functionality set forth in the publications incorporated by reference above. Certain features of dialysis fluid circuit 70 are illustrated in FIG. 1. In the illustrated embodiment, dialysis fluid circuit 70 includes a to-blood filter dialysis fluid pump 64. Pump 64 is in one embodiment configured the same as blood pump 30. Pump 64, like pump 30, includes a pair of pump pods, which again may be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump chamber 96 operating with valves 98i and 98o located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, may be single pod pumps because continuous pumping is not as important in mixing line 62 because there is a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when an HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a tube. If so, the system valves may still be actuated pneumatically according to the features of the present disclosure.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are not illustrated but are disclosed in detail in the publications incorporated by reference above.

FIG. 1 also illustrates that dialysis fluid is pumped along a fresh dialysis fluid line 76, through a heater 78 and an ultrafilter 80, before reaching blood filter 40, after which used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering bugs or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural dialysis fluid valves, and a dialysis fluid holding tank, all illustrated and described in detail in the publications incorporated by reference above.

In the illustrated embodiment, hemodialysis system 10 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months.

In alternative embodiments, or for CRRT for example, multiple bags of sterilized dialysis fluid or infusate are ganged together and used one after another. In such a case, the emptied supply bags can serve as drain or spent fluid bags.

The machine 90 of system 10 includes an enclosure as indicated by the dotted line of FIG. 1. The enclosure of machine 90 varies depending upon the type of treatment, whether the treatment is in-center or a home treatment, and whether the dialysis fluid/infusate supply is a batch-type (e.g., bagged) or on-line.

FIG. 2 illustrates that machine 90 of system 10 of FIG. 1 may operate with a blood set 100. Blood set 100 includes arterial line 14, venous line 16, heparin vial 24, heparin pump 26/blood pump 30 and blood filter 40 (e.g., dialyzer). An airtrap 110 may be located in venous line 16 to remove air from the blood before being returned to patient 12. As discussed herein, high temperature air detectors 22a and 22v contact and thereby operate with arterial and venous lines 14 and 16, respectively.

In FIGS. 1 and 2, any of pumps 26, 30 (30a and 30b), 64, 96 (and other pumps not illustrated) and any of the valves, such as valves 32i, 32o, 34i, 34o, 68i, 68o, 98i, and 98o may be pneumatically actuated. In an embodiment, each of the pumps and valves has a fluid side and an air side, separated by a flexible membrane. Negative pneumatic pressure may be applied to the air side of the membrane to draw fluid into a pump chamber or to open a valve (or pump or valve could be opened by venting positive closing pressure to atmosphere and allowing fluid pressure to open). Positive pneumatic pressure is applied to the air side of the membrane to expel fluid from a pump chamber or to close a valve.

Figure 3A:
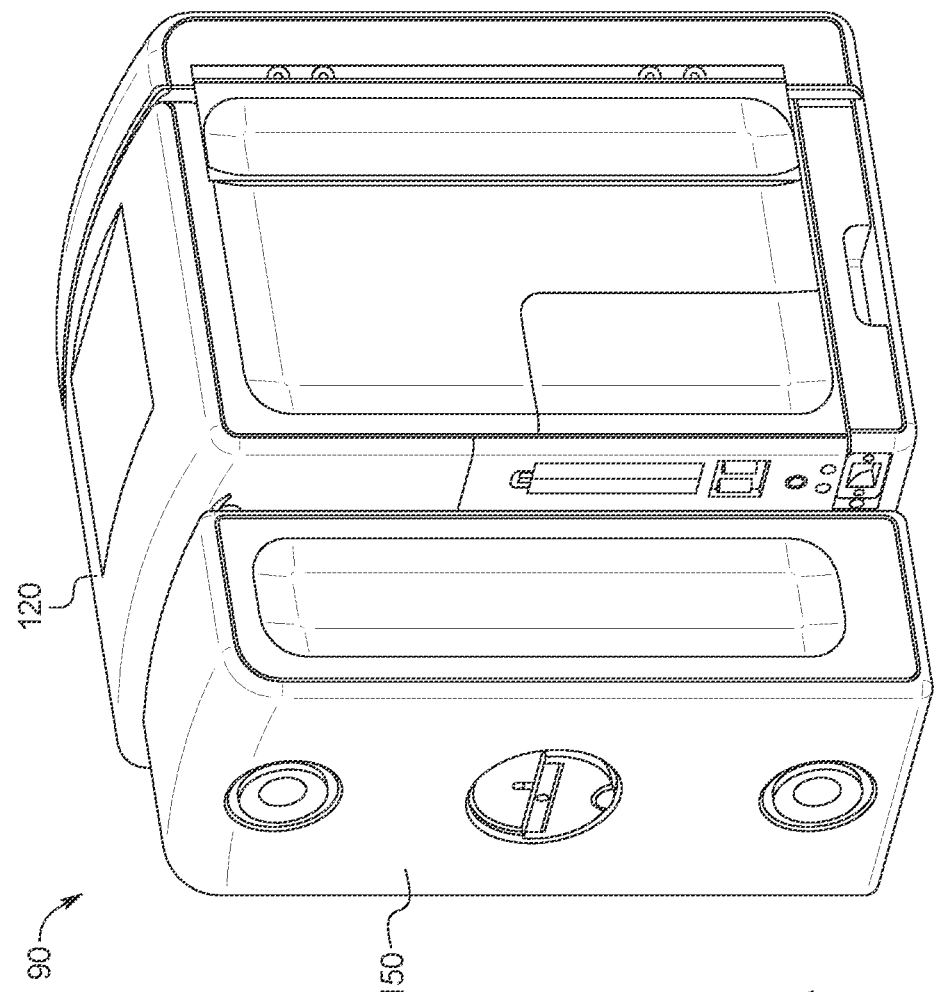
FIG. 3A is a perspective view of one embodiment of the renal failure therapy machine of FIG. 1 with a pump box connected to a main chassis of the machine.

Referring now to FIG. 3A, an embodiment of a medical fluid delivery machine 90, such as an HD machine, is illustrated. Medical fluid delivery machine 90 in the illustrated embodiment includes a medical fluid delivery chassis 120 connected to a pneumatic pump box 150. Pump box 150 holds pneumatic pumping equipment, such as a compressor and associated dryer, vacuum pump, at least one positive pressure accumulator and at least one negative pressure accumulator. In an embodiment, pneumatic pump box 150 is connected removeably to medical fluid delivery chassis 120, so that the pump box can be moved away from the patient (e.g., placed in a closet) to reduce noise in the treatment area near the patient. At least one positive pneumatic line, at least one negative pneumatic line, and at least one power line (FIG. 3B) run from pneumatic pump box 150 to medical fluid delivery chassis 120 to drive pumps 26, 30 (30a and 30b), 64, 96 (and other pumps not illustrated) and any of the valves, such as valves 32i, 32o, 34i, 34o, 68i, 68o, 98i and 98o, which are located within or are mounted onto medical fluid delivery chassis 120.

Figure 3B:
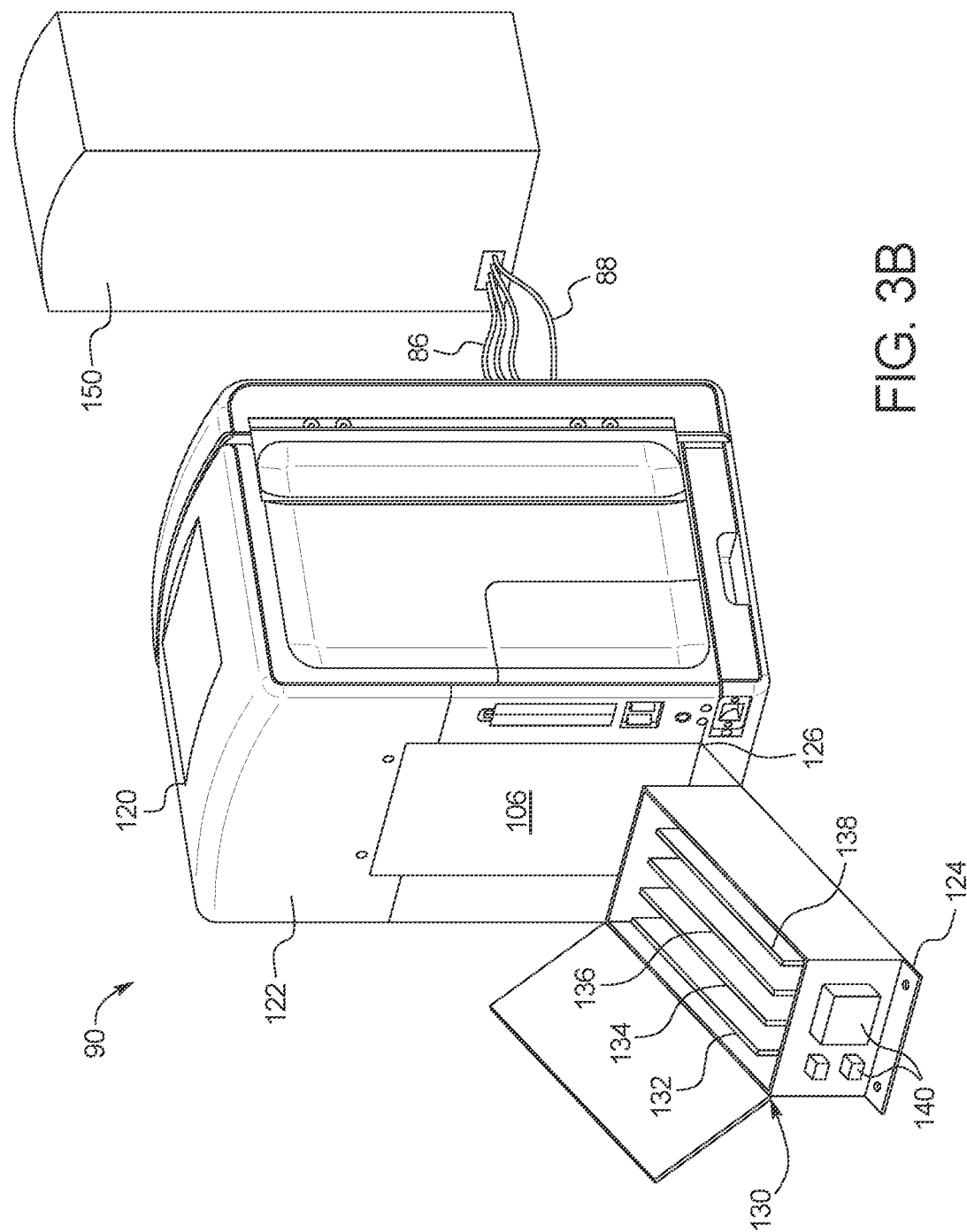
FIG. 3B is a perspective view of the renal failure therapy machine of FIG. 3A, with the pump box removed so that a service door may be opened to allow for the electronics of the machine to rotate out of the machine for servicing.

Referring now to FIG. 3B, medical fluid delivery machine is illustrated with pump box 150 removed. As discussed above, removed pump box 150 remains in pneumatic and operable communication with medical fluid delivery chassis 120 via extended pneumatic lines 86 and extended power lines 88. The removed pump box exposes a backside 122 of medical fluid delivery chassis 120 and an access door 124. Access door 124 in the illustrated embodiment rotates open along a bottom hinge 126. In an alternative embodiment, access door 124 may be translated away from backside 122 via tracks in a drawer-like manner. In either case, removing access door 124 exposes an electronics cage 130 (shown with its door open to see inside).

Electronics cage 130 holds multiple printed circuit boards ("PCB's"), such as PCB's 132, 134, 136 and 138, and other electrical equipment of machine 90. Electronics cage 130 is made of a material, such as, high temperature plastic, steel, or stainless steel, which shields PCB's 132, 134, 136 and 138, and other electrical equipment of machine 90 from the heat generated within the machine, e.g., from heater 78 and the fluid carrying equipment within machine 90 subjected to heat disinfection. One electrical component that is not held within electronics cage 130 is power supply 140 and associated transformers, which themselves generate heat. Power supply 140 in the illustrated embodiment (and associated transformers which may be internal to the power supply housing) is mounted instead to the top of electronics cage 130. By doing so, heat generated by power supply 140 does not become trapped within electronics cage 130. It has been found that elevating the temperature of components on a PCB by 10° C. may reduce their service life by half.

Hinging electronics cage 130 out of the way as illustrated in FIG. 3B provides a number of benefits. First, electronics cage 130 enables PCB's 132, 134, 136 and 138, and other electrical equipment of machine 90 to be held in place firmly, increasing reliability. Removable electronics cage 130 also improves the serviceability of machine 90, regarding both the contents of cage 130 any by opening up an interior space 106 within machine 90, allowing better access to other machine components. The components of pump box 150 are also readily accessible due to its removability.

Figure 4A:
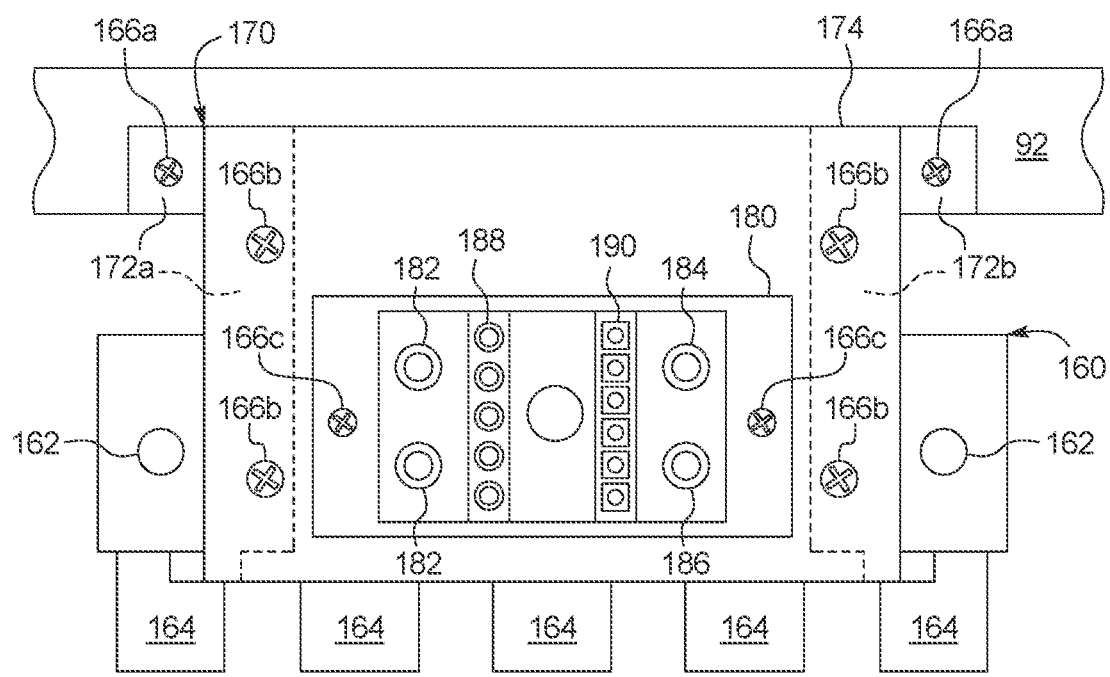
FIGS. 4A and 4B are front and bottom views, respectively, of one embodiment of a pneumatic manifold mounting regime that includes a removable faceplate to enable access to various pneumatic valves connected to the pneumatic manifold.
Figure 4B:
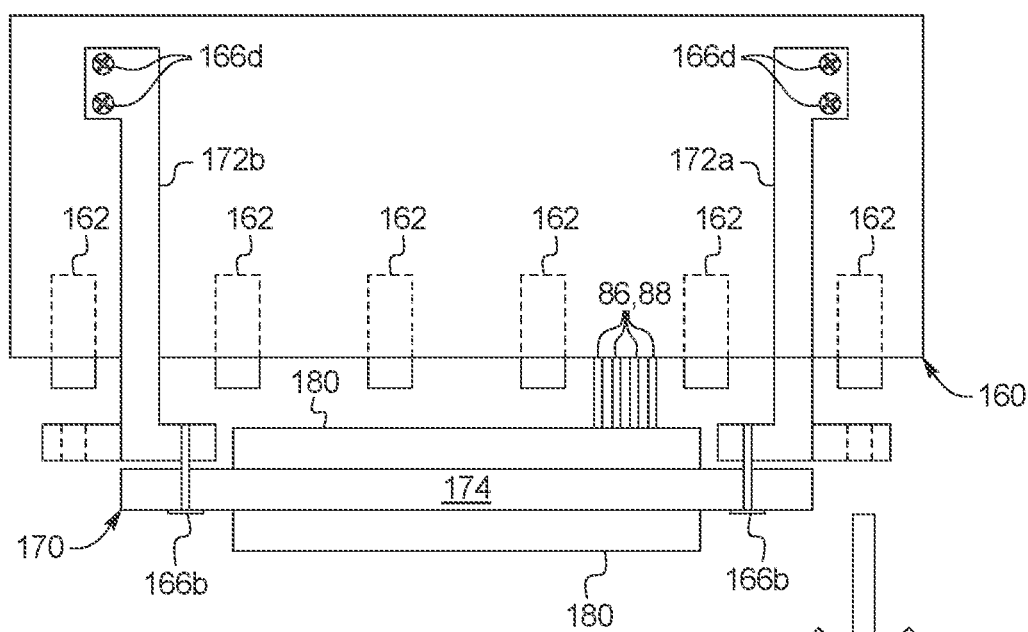

Referring now to FIGS. 4A and 4B, in an embodiment, pneumatic components, such as, pneumatic regulators, electrically actuated binary solenoid valves, and electrically actuated variable pneumatic (vari-valves) are located on a pneumatic manifold 160. In the illustrated embodiment, manifold 160 pneumatically is sealed to electrically actuated binary solenoid valves 162, and electrically actuated variable pneumatic (vari-valves) 164.

Pneumatic manifold 160 is mounted within machine 90 via a mounting assembly 170 fixed to frame 92 of machine 90. Mounting assembly 170 includes a fixed portion having first and second mounting flanges 172a and 172b. First and second mounting flanges 172a and 172b are fastened to frame 92 of machine 90 via fasteners 166a. Mounting assembly 170 includes a removable portion in the form of a faceplate 174, which mounts removeably to first and second mounting flanges 172a and 172b via fasteners 166b. Mounting flanges 172a and 172b and removable faceplate 174 may be made of metal, for example, stainless steel or aluminum. Mounting flanges 172a and 172b in turn mount to pneumatic manifold 160 from underneath via fasteners 166d.

Removable faceplate 174 in turn supports one or more quick disconnect plate 180, which is attached to faceplate 174 via fasteners 166c. Quick disconnect plate 180 provides quick disconnect connections to machine 90 for first and second vacuum lines via sockets 182, low positive pressure via socket 184, high positive pressure via socket 186, AC power via sockets 188, and DC power via sockets 190. Pneumatic quick disconnect sockets 182, 184 and 186 are in pneumatic communication with various components of pneumatic manifold 160 via pneumatic lines 86 as illustrated in FIG. 4B. Electrical power quick disconnect sockets 188 and 190 are in electrical communication with multiple electrical components within machine 90, including components of pneumatic manifold 160, via electrical lines 88 as illustrated in FIG. 4B.

Pneumatic lines 86 may be rigid or flexible. Regardless, they in combination with electrical lines 88 provide enough slack such that faceplate 174 and corresponding quick disconnect plate 180 may be moved out of the way of pneumatic manifold 160 if needed, e.g., to replace a binary valve 162. As illustrated in FIGS. 4A and 4B, binary valves 162 on the ends of pneumatic manifold 160 may be accessible with faceplate 174 in place, however, the binary valves 162 hidden behind faceplate 174 are not accessible. Without removable faceplate 174, If any of those valves 162 needs replacement, mounting assembly 170 and pneumatic manifold 160 have to be removed from frame 92 via removing fasteners 166a, and then mounting assembly 170 needs to be removed from pneumatic manifold 160 by removing fasteners 166d. Removable faceplate 174 instead allows any of binary valves 162 to be replaced easily, e.g., by pulling them in the direction of the arrow in FIG. 4B, while leaving mounting assembly 170 and pneumatic manifold 160 intact.

Referring now to FIGS. 5 to 8, one embodiment for mounting vari-valves 164 to pneumatic manifold 160 (FIG. 4A) is illustrated. One goal for the mounting of any of the pneumatic valves is to prevent particulate from entering the pneumatic pathways 168 of pneumatic manifold 160. It has been found that attaching the valves, such as vari-valves 164, to pneumatic manifold 160 by threaded interfaces may cause particulate to shear off of the threads of pneumatic manifold 160 and fall into the pneumatic pathways 168, which are then pushed or pulled by air in the pathways into a pneumatic component, where the particulate can cause damage and/or malfunction. Especially where the threads of the valve are stainless steel and manifold 160 is a softer metal, such as aluminum (which is conducive to all of the machining involved with the plated of manifold), the threading action can shear particles, shavings or coatings from the threads of manifold 160.

Figure 6:
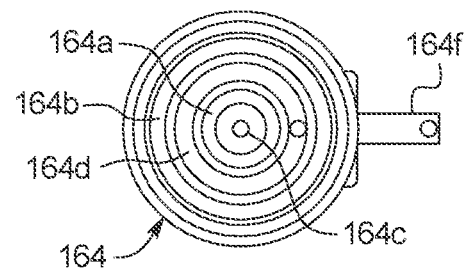

FIG. 6 illustrates the bottom side of vari-valve 164 having inner and outer o-rings 164a and 164b, a pneumatic inlet 164c, and an annular pneumatic outlet 164d. Inner o-ring 164a seals pneumatic inlet 164c, while inner and outer o-rings 164a and 164b collectively seal annular pneumatic outlet 164d. O-rings 164a and 164b accordingly need to be compressed to properly mount vari-valve 164.

Figure 5:
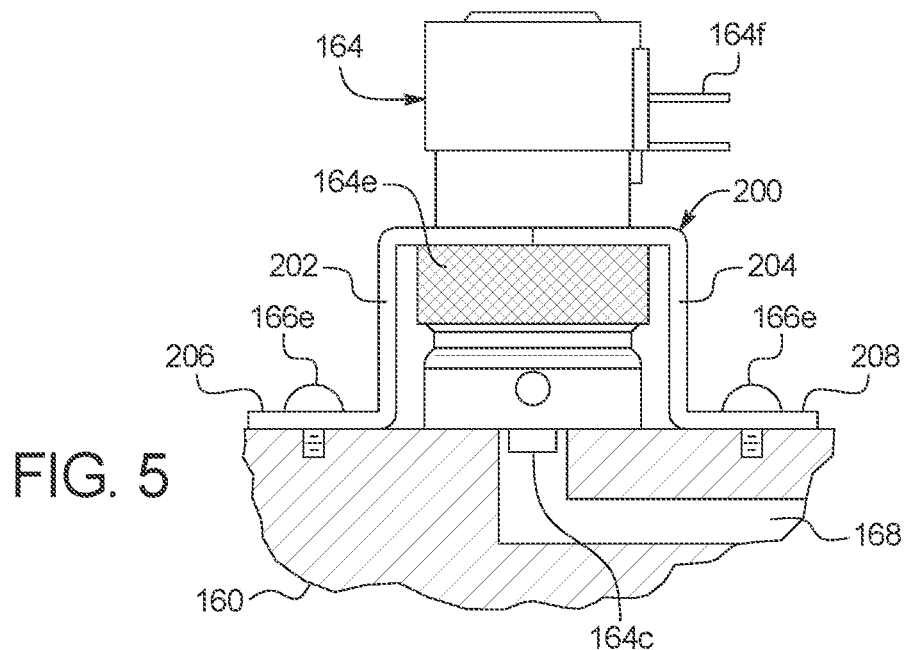
FIGS. 5 to 8 illustrate a first embodiment for mounting pneumatic valves to a plate of the pneumatic manifold of the present disclosure.

FIG. 5 illustrates one embodiment of a bracket 200 (referring collectively to brackets 200a and 200b in FIGS. 7 and 8), which clamps to and seals vari-valve 164 to pneumatic manifold 160. In the illustrated embodiment, bracket 200 includes a first bracket member 202 and a second bracket 204 (referring collectively to bracket members 202a/202b and 204a/204b in FIGS. 7 and 8). Bracket members 202 and 204 are bent or formed so as to fit over and around and engage the top of a larger, intermediate diameter portion 164e of vari-valve 164. Clamping bracket 200 to an intermediate diameter portion 164e of vari-valve 164 enables an upper, electrical connection portion 164f of vari-valve 164 to remain exposed for connection to associated electrical wiring.

Bracket 200 may be made of metal, such as stainless steel or treated steel. Bracket 200 may be made alternatively of a touch plastic, such as teflon. Sidewalls of bracket 200 in FIG. 5 have been removed to show how bracket members 202 and 204 come together at least substantially all the way around the larger, intermediate diameter portion 164e of vari-valve 164. Bracket 200 (including brackets 200a and 200b) however may have sidewalls and/or gussets as necessary to prevent bracket 200 from bending when placed under mounting stress to compress o-rings 164a and 164b.

Figure 7:
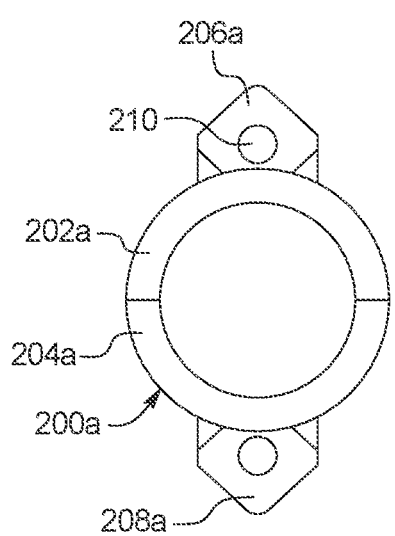
Figure 8:
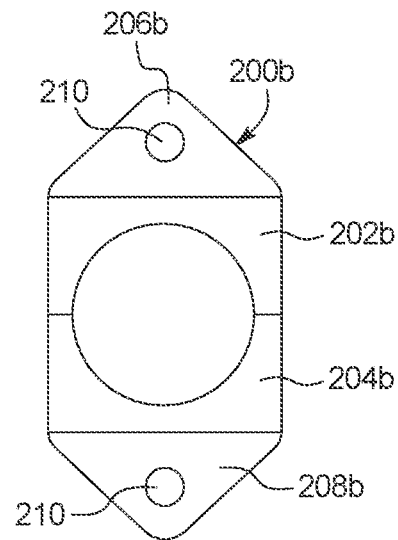

Bracket 200 (including brackets 200a and 200b) includes flanges 206 and 208 (referring collectively to bracket member flanges 206a/206b and 208a/208b in FIGS. 7 and 8). Flanges 206 and 208 each define an aperture 210 for receiving a fastener 166e. In the illustrated embodiment of FIG. 5, fasteners 166e threadingly engage pneumatic manifold 160 to clamp flanges 206 and 208 and associated bracket members 202 and 204 to intermediate diameter portion 164e of vari-valve 164, thereby compressing o-rings 164a and 164b.

FIGS. 7 and 8 illustrated different example shapes for bracket 200 (including brackets 200a and 200b). Bracket 200a is rounded with cylindrical sides (not seen) and may be more easily produced via molding, e.g., of tough plastic. Bracket 200b is square with straight sides (not seen) and may be formed easily from metal. It should be appreciated that each of brackets 200a and 200b is configured to distribute force evenly about intermediate diameter portion 164e of vari-valve 164. It should also be appreciated that brackets 200a and 200b are not limited to mounting valves, such as vari-valve 164, and may be used instead to mount other structures sealingly to a manifold, such as pneumatic manifold 160, including binary valves, pressure gauges, pressure regulators, flowmeters, filters, piping and tubing and associated fittings, and the like.

Figure 9A:
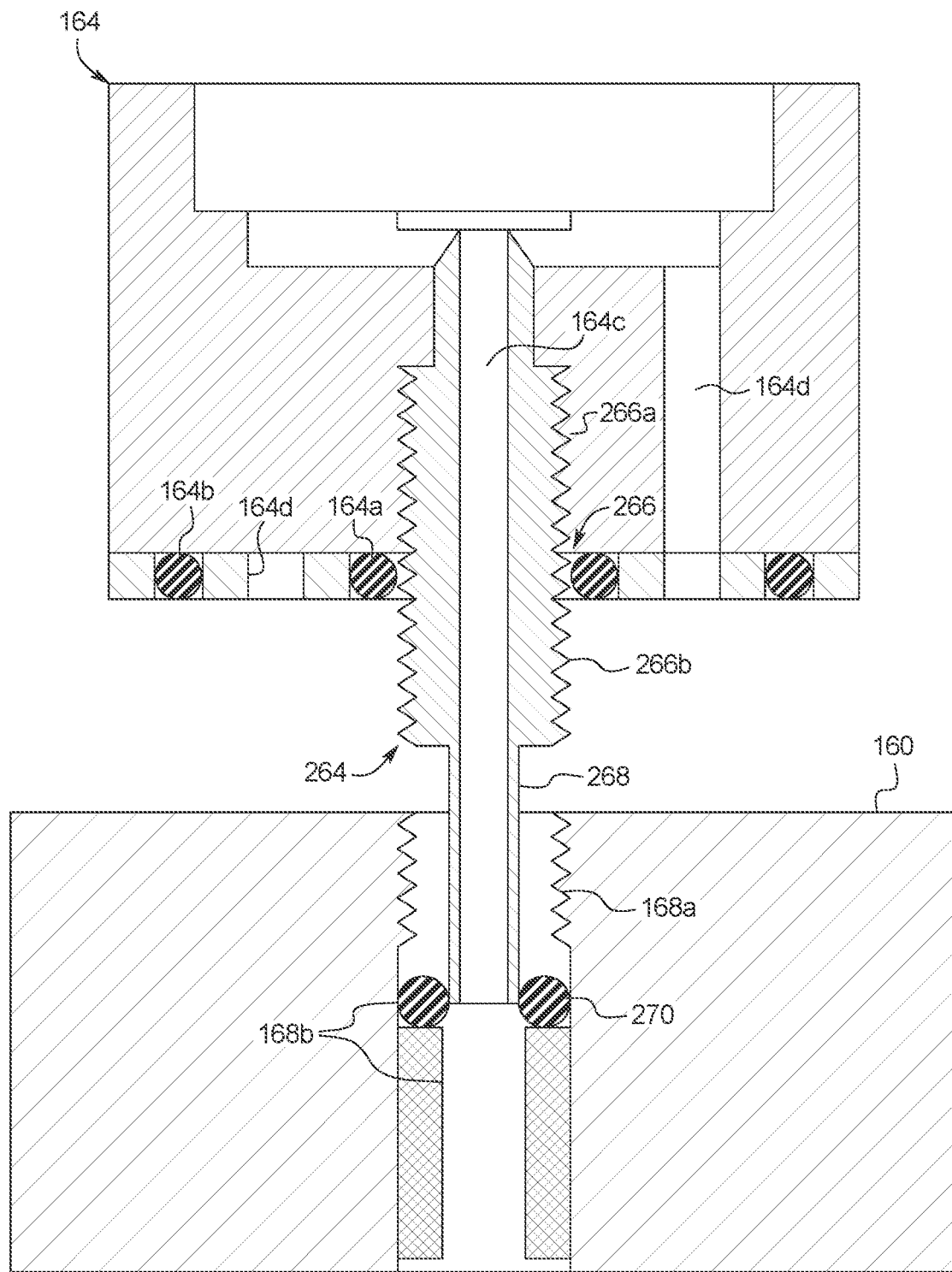
FIGS. 9A and 9B illustrate a second embodiment for mounting pneumatic valves to a plate of the pneumatic manifold of the present disclosure.
Figure 9B:
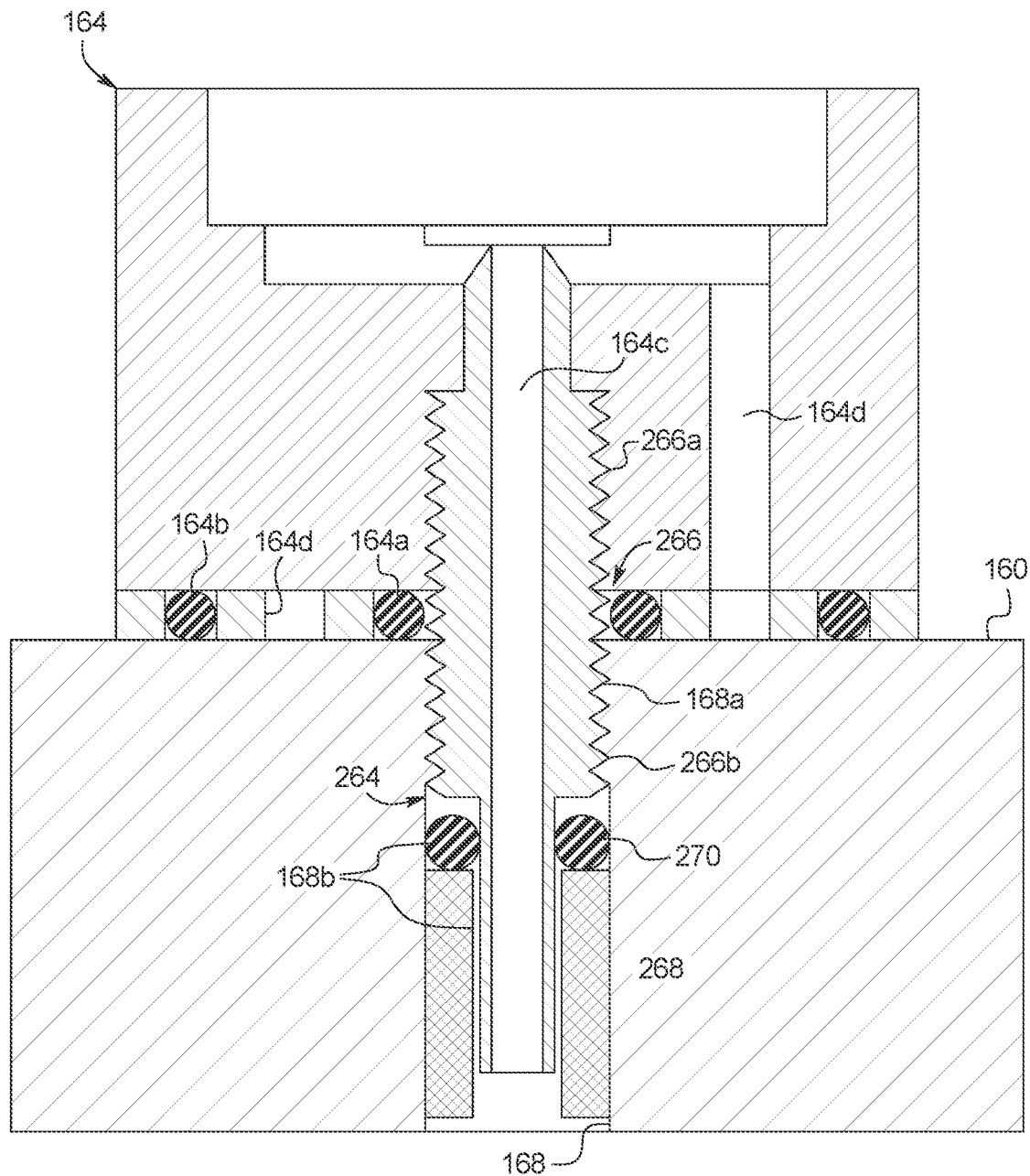

Referring now to FIGS. 9A and 9B, other mounting scenarios for mounting vari-valve 164 are illustrated. Vari-valve 164 as discussed above includes inner and outer o-rings 164a and 164b, a pneumatic inlet 164c, and an annular pneumatic outlet 164d. Inner o-ring 164a seals pneumatic inlet 164c, while inner and outer o-rings 164a and 164b collectively seal annular pneumatic outlet 164d. Vari-valve includes a port 264 that extends into pneumatic pathway 168 of pneumatic manifold 160. Port 264 includes an upper threaded portion 266 and a lower smooth portion 268. Upper threaded portion 266 and a lower smooth portion 268 are made of stainless steel in one embodiment. Upper threaded portion 266 in the illustrated embodiment includes male threads 266a that thread up into the body of valve and male threads 266b angled in the reverse direction that thread down into pneumatic pathway 168 of pneumatic manifold 160.

Pneumatic pathway 168 includes an upper mating female threaded portion 168a and a lower mating smooth portion 168b. In FIG. 9A, lower smooth portion 168b is formed in part by an insert press-fitted into pneumatic manifold 160. In FIG. 9B, lower smooth portion 168b is formed directly in one or more of the plates of pneumatic manifold 160. In either case, the top of lower smooth portion 168b forms a step upon which a third o-ring 270 is placed. The step prevents o-ring 270 from being pushed down into pneumatic pathway 168.

The length of port 264 and its lower smooth portion 268 in combination with the placement of the step and o-ring 270 ensure that lower smooth portion 268 contacts and compresses o-ring 270 to lower smooth portion 168b prior to male threads 266b engaging upper mating female threaded portion 168a of pneumatic pathway 168. In this way, a sealed chamber is created prior to creation of, and that therefore catches, any chips or particulate that are sheared off of female threaded portion 168a of pneumatic pathway 168. The chips or particulate therefore cannot fall further into pneumatic pathway 168.

FIG. 9A illustrates lower smooth portion 268 just beginning to contact and compress o-ring 270 against the wall of pneumatic pathway 168. FIG. 9B illustrates vari-valve 164 fully threaded into pneumatic manifold 160. In FIG. 9B, any chips or particulate that are sheared off of female threaded portion 168a of pneumatic pathway 168 due to the threaded connection fall on top of compressed o-ring 270 or against the small exposed section of lower smooth portion 268, but not further down into pneumatic pathway 168.

It should be appreciates that while port 264 is illustrated as being part of vari-valve 164, port 264 may be used instead to mount other structures sealingly to a manifold, such as pneumatic manifold 160, including binary valves, pressure gauges, pressure regulators, flowmeters, filters, piping and tubing and associated fittings, and the like.

Figure 10:
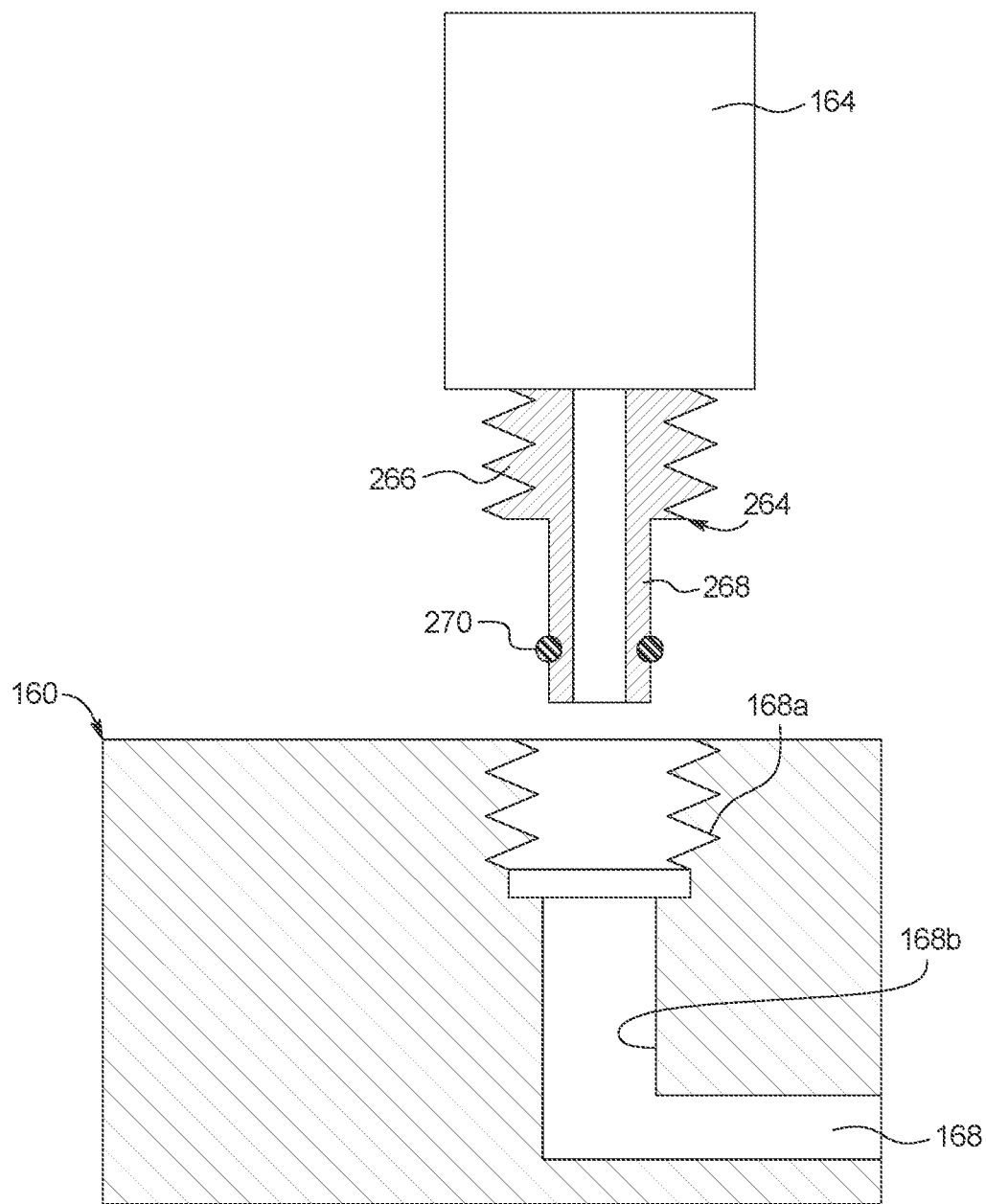
FIG. 10 illustrates a third embodiment for mounting pneumatic valves to a plate of the pneumatic manifold of the present disclosure.

Referring now to FIG. 10 a further alternative mounting scenario for any type of pneumatic component, such as vari-valves 164, binary valves, pressure gauges, pressure regulators, flowmeters, filters, piping and tubing and associated fittings, is illustrated. An attachment mechanism 220 includes a port 264 as described below that attaches to a body. The body may be a body of any of vari-valve 164, a binary valve body, a pressure gauge body, a pressure regulator body, a flowmeter body, a filter body, piping, tubing and/or associated fittings. For purposes of illustration, the body will be described hereafter as that of vari-valve 164

Vari-valve 164 as discussed and illustrated above includes inner and outer o-rings 164a and 164b, a pneumatic inlet 164c, and an annular pneumatic outlet 164d. Inner o-ring 164a seals pneumatic inlet 164c, while inner and outer o-rings 164a and 164b collectively seal annular pneumatic outlet 164d. Vari-valve 164 again includes a port 264 that extends into pneumatic pathway 168 of pneumatic manifold 160. Port 264 includes an upper threaded portion 266 and a lower smooth portion 268 extending from upper threaded portion 266. Upper threaded portion 266 and lower smooth portion 268 are made of stainless steel, steel, titanium, aluminum, alloys and combinations thereof in various embodiments.

Pneumatic pathway 168 includes an upper mating female threaded portion 168a and a lower mating smooth portion 168b. In FIG. 10, lower smooth portion 168b is formed directly in one or more of the plates of pneumatic manifold 160. As opposed to FIGS. 9A and 9B, o-ring 270 is here positioned into a mating groove of lower smooth portion 268 of valve 164.

The length of port 264 and its lower smooth portion 268 in combination with the placement of o-ring 270 onto lower smooth portion 268 ensure that o-ring 270 passes through female threads 168a and contacts and compresses to lower smooth portion 168b prior to male threads 266 engaging upper mating female threaded portion 168a of pneumatic pathway 168. Here again, a sealed chamber is created prior to the creation of, and that therefore catches and traps, any chips or particulates that are sheared off of female threaded portion 168a of pneumatic pathway 168 or male threaded portion 266 of port 264. The chips or particulates therefore cannot fall further into pneumatic pathway 168.

While the valves of FIGS. 9A, 9B and 10 are described as being pneumatic valves, the valves may alternatively operate with other types of systems, such as water, hydraulic or oil-based systems. The valves may alternatively be hydraulic valves, for example. The connection structures of FIGS. 6 to 10 may therefore be used to prevent the transfer of particulates created when threading mating elements of any pneumatic, hydraulic, water or oil-based system from entering the flow path of the system.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A connection apparatus for sealing to a pathway of a mounting structure, the connection apparatus comprising:
a body; and
a port including a threaded portion extending from the body and a non-threaded portion extending from the threaded portion, the non-threaded portion carrying a gasket, the gasket positioned along the non-threaded portion such that the mounting structure to which the connection apparatus is mounted contacts the gasket prior to the threaded portion engaging a mating threaded portion of the mounting structure, the port providing fluid communication between the body and the pathway of the mounting structure, and wherein the gasket is configured to create a seal between the pathway and both the threaded portion and mating threaded portion after engagement.

2. The connection apparatus of claim 1, wherein the body is a valve body, the valve body configured to be electrically actuated to open or close a fluid passageway.

3. The connection apparatus of claim 1, wherein the non-threaded portion defines a groove that accepts the gasket.

4. The connection apparatus of claim 1, wherein the body includes a surface, the port extending from the surface, the surface defining an aperture spaced apart from the port, the gasket is a first gasket, and wherein the valve body includes a second gasket extending around the spaced-apart aperture.

5. The connection apparatus of claim 1, which is configured for use with a pneumatic system.

6. The connection apparatus of claim 1, wherein the body is a variable orifice valve body.

7. The connection apparatus of claim 1, which is configured for use with a water system.

8. The connection apparatus of claim 1, which is configured for use with an oil-based system.

9. The connection apparatus of claim 1, wherein the body is a binary valve body.

10. The connection apparatus of claim 1, wherein the body is a pressure gauge body.

11. The connection apparatus of claim 1, wherein the body is a pressure regulator body.

12. The connection apparatus of claim 1, wherein the body is a flowmeter body.

13. The connection apparatus of claim 1, wherein the body is a filter body.

14. The connection apparatus of claim 1, wherein the body is piping.

15. The connection apparatus of claim 1, wherein the body is tubing.

16. The connection apparatus of claim 1, wherein the body is a piping/tubing fitting.

* * * * *